US011478351B2

(12) United States Patent
Rowe et al.

(10) Patent No.: US 11,478,351 B2
(45) Date of Patent: Oct. 25, 2022

(54) HEART SHAPE PRESERVING ANCHOR

(71) Applicant: Edwards Lifesciences Corporation, Irvine, CA (US)

(72) Inventors: Stanton J. Rowe, Newport Coast, CA (US); Yaron Keidar, Kiryat Ono (IL)

(73) Assignee: Edwards Lifesciences Corporation, Irvine, CA (US)

( * ) Notice: Subject to any disclaimer, the term of this patent is extended or adjusted under 35 U.S.C. 154(b) by 94 days.

(21) Appl. No.: 16/934,401

(22) Filed: Jul. 21, 2020

(65) Prior Publication Data
US 2020/0352718 A1 Nov. 12, 2020

Related U.S. Application Data

(63) Continuation of application No. PCT/US2019/014554, filed on Jan. 22, 2019.

(60) Provisional application No. 62/620,367, filed on Jan. 22, 2018.

(51) Int. Cl.
*A61F 2/24* (2006.01)
(52) U.S. Cl.
CPC .......... *A61F 2/2457* (2013.01); *A61F 2/2487* (2013.01); *A61F 2210/009* (2013.01); *A61F 2230/0067* (2013.01)
(58) Field of Classification Search
CPC ...... A61F 2/246; A61F 2/2418; A61F 2/2454; A61F 2/2412; A61F 2/2457; A61F 2/2409; A61F 2/2487; A61F 2230/0093; A61F 2/24; A61F 2/2478; A61B 2017/00243; A61B 17/0401
See application file for complete search history.

(56) References Cited

U.S. PATENT DOCUMENTS

| | | | |
|---|---|---|---|
| 3,671,979 | A | 6/1972 | Moulopoulos |
| 3,689,942 | A | 9/1972 | Rapp |
| 3,898,701 | A | 8/1975 | La Russa |
| 4,306,319 | A | 12/1981 | Kaster |
| 4,407,271 | A | 10/1983 | Schiff |
| 5,167,239 | A | 12/1992 | Cohen et al. |
| 5,332,402 | A | 7/1994 | Teitelbaum |
| 5,397,351 | A | 3/1995 | Pavcnik et al. |
| 5,554,184 | A | 9/1996 | Machiraju |
| 5,607,465 | A | 3/1997 | Camilli |
| 5,735,842 | A | 4/1998 | Krueger et al. |

(Continued)

FOREIGN PATENT DOCUMENTS

| | | |
|---|---|---|
| EP | 1472996 A1 | 11/2004 |
| FR | 2728457 A1 | 6/1996 |

(Continued)

*Primary Examiner* — Seema Mathew
(74) *Attorney, Agent, or Firm* — Knobbe Martens Olson & Bear LLP

(57) ABSTRACT

Embodiments of a heart shape preserving anchor are disclosed herein. The heart shape preserving anchor can include a frame having one or more wings extending from a lower end of the frame. The frame can be sized and shaped to distribute forces over a large surface area thereby reducing pressures applied on the heart. The anchor can include a tether for coupling to a prosthesis, such as a replacement heart valve prosthesis. In some embodiments, the anchor can include a tether adjustment mechanism which can be wirelessly operated to adjust a length of the tether relative to the frame.

20 Claims, 14 Drawing Sheets

(56) References Cited

U.S. PATENT DOCUMENTS

| | | | |
|---|---|---|---|
| 5,957,949 A | 9/1999 | Leonhardt et al. | |
| 5,961,440 A * | 10/1999 | Schweich, Jr. | A61F 2/2487 600/16 |
| 6,050,972 A | 4/2000 | Zadno-Azizi et al. | |
| 6,210,432 B1 | 4/2001 | Solem et al. | |
| 6,214,029 B1 * | 4/2001 | Thill | A61B 17/0057 606/213 |
| 6,217,567 B1 | 4/2001 | Zadno-Azizi et al. | |
| 6,287,334 B1 | 9/2001 | Moll et al. | |
| 6,290,674 B1 * | 9/2001 | Roue | A61B 17/12122 604/107 |
| 6,312,464 B1 | 11/2001 | Navia | |
| 6,332,893 B1 | 12/2001 | Mortier et al. | |
| 6,358,277 B1 | 3/2002 | Duran | |
| 6,482,228 B1 | 11/2002 | Norred | |
| 6,540,782 B1 | 4/2003 | Snyders | |
| 6,602,288 B1 | 8/2003 | Cosgrove et al. | |
| 6,605,112 B1 | 8/2003 | Moll et al. | |
| 6,629,534 B1 | 10/2003 | St. Goar et al. | |
| 6,709,456 B2 | 3/2004 | Langberg et al. | |
| 6,730,121 B2 | 5/2004 | Ortiz et al. | |
| 6,752,813 B2 | 6/2004 | Goldfarb et al. | |
| 6,764,510 B2 | 7/2004 | Vidlund et al. | |
| 6,767,362 B2 | 7/2004 | Schreck | |
| 6,790,231 B2 | 9/2004 | Liddicoat et al. | |
| 6,797,002 B2 | 9/2004 | Spence et al. | |
| 6,808,483 B1 | 10/2004 | Ortiz et al. | |
| 6,869,444 B2 | 3/2005 | Gabbay | |
| 6,875,224 B2 | 4/2005 | Grimes | |
| 6,994,092 B2 | 2/2006 | van der Burg et al. | |
| 7,004,958 B2 | 2/2006 | Adams et al. | |
| 7,011,669 B2 | 3/2006 | Kimblad | |
| 7,011,682 B2 | 3/2006 | Lashinski et al. | |
| 7,018,406 B2 | 3/2006 | Seguin et al. | |
| 7,070,616 B2 | 7/2006 | Majercak et al. | |
| 7,077,862 B2 | 7/2006 | Vidlund et al. | |
| 7,160,322 B2 | 1/2007 | Gabbay | |
| 7,175,656 B2 | 2/2007 | Khairkhahan | |
| 7,217,287 B2 | 5/2007 | Wilson et al. | |
| 7,226,467 B2 | 6/2007 | Lucatero et al. | |
| 7,252,682 B2 | 8/2007 | Seguin | |
| 7,291,168 B2 | 11/2007 | Macoviak et al. | |
| 7,303,526 B2 * | 12/2007 | Sharkey | A61B 17/12122 623/910 |
| 7,320,665 B2 | 1/2008 | Vijay | |
| 7,322,957 B2 | 1/2008 | Kletschka et al. | |
| 7,381,220 B2 | 6/2008 | Macoviak et al. | |
| 7,404,824 B1 | 7/2008 | Webler et al. | |
| 7,559,936 B2 | 7/2009 | Levine | |
| 7,678,145 B2 | 3/2010 | Vidlund et al. | |
| 7,758,596 B2 | 7/2010 | Oz et al. | |
| 7,785,366 B2 | 8/2010 | Maurer et al. | |
| 7,815,580 B2 | 10/2010 | Viswanathan | |
| 7,854,762 B2 | 12/2010 | Speziali et al. | |
| 7,887,477 B2 * | 2/2011 | Nikolic | A61B 17/12122 600/16 |
| 7,901,454 B2 | 3/2011 | Kapadia et al. | |
| 7,927,370 B2 | 4/2011 | Webler et al. | |
| 7,942,928 B2 | 5/2011 | Webler et al. | |
| 8,007,428 B2 | 8/2011 | Vijay | |
| 8,052,751 B2 | 11/2011 | Aklog et al. | |
| 8,070,805 B2 | 12/2011 | Vidlund et al. | |
| 8,092,525 B2 | 1/2012 | Eliasen et al. | |
| 8,133,213 B2 | 3/2012 | Lashinski | |
| 8,172,856 B2 | 5/2012 | Eigler et al. | |
| 8,216,302 B2 | 7/2012 | Wilson et al. | |
| 8,348,963 B2 | 1/2013 | Wilson | |
| 8,403,983 B2 | 3/2013 | Quadri et al. | |
| 8,414,644 B2 | 4/2013 | Quadri et al. | |
| 8,449,606 B2 | 5/2013 | Eliasen et al. | |
| 8,460,370 B2 | 6/2013 | Zakay | |
| 8,486,136 B2 | 7/2013 | Maurer et al. | |
| 8,579,967 B2 | 11/2013 | Webler et al. | |
| 8,652,203 B2 | 2/2014 | Quadri et al. | |
| 8,758,430 B2 | 6/2014 | Ferrari et al. | |
| 8,758,432 B2 | 6/2014 | Solem | |
| 8,778,017 B2 | 7/2014 | Eliasen et al. | |
| 8,784,482 B2 | 7/2014 | Rahdert et al. | |
| 8,845,717 B2 | 9/2014 | Khairkhahan et al. | |
| 8,888,843 B2 | 11/2014 | Khairkhahan et al. | |
| 8,888,844 B2 | 11/2014 | Eliasen et al. | |
| 8,932,348 B2 | 1/2015 | Solem et al. | |
| 8,968,395 B2 | 3/2015 | Hauser et al. | |
| 9,161,837 B2 | 10/2015 | Kapadia | |
| 9,232,998 B2 | 1/2016 | Wilson et al. | |
| 9,232,999 B2 | 1/2016 | Maurer et al. | |
| 9,259,317 B2 | 2/2016 | Wilson et al. | |
| 9,289,297 B2 | 3/2016 | Wilson et al. | |
| 9,474,605 B2 | 10/2016 | Rowe et al. | |
| 9,579,199 B2 | 2/2017 | Hauser et al. | |
| 9,636,223 B2 | 5/2017 | Khalil et al. | |
| 9,681,951 B2 | 6/2017 | Ratz et al. | |
| 10,583,009 B2 | 3/2020 | Hauser et al. | |
| 2001/0021872 A1 | 9/2001 | Bailey et al. | |
| 2001/0037129 A1 * | 11/2001 | Thill | A61B 17/0057 606/213 |
| 2002/0013571 A1 * | 1/2002 | Goldfarb | A61B 17/0625 606/1 |
| 2002/0128708 A1 | 9/2002 | Northrup et al. | |
| 2002/0198594 A1 | 12/2002 | Schreck | |
| 2003/0050682 A1 | 3/2003 | Sharkey | |
| 2003/0050694 A1 | 3/2003 | Yang et al. | |
| 2003/0078654 A1 | 4/2003 | Taylor et al. | |
| 2003/0120341 A1 | 6/2003 | Shennib et al. | |
| 2003/0187494 A1 | 10/2003 | Loaldi | |
| 2004/0019378 A1 | 1/2004 | Hlavka et al. | |
| 2004/0024414 A1 | 2/2004 | Downing | |
| 2004/0092858 A1 | 5/2004 | Wilson et al. | |
| 2004/0098081 A1 | 5/2004 | Landreville et al. | |
| 2004/0117032 A1 | 6/2004 | Roth | |
| 2004/0143294 A1 * | 7/2004 | Corcoran | A61B 17/0057 606/213 |
| 2004/0167539 A1 | 8/2004 | Kuehn et al. | |
| 2004/0193259 A1 | 9/2004 | Gabbay | |
| 2004/0225233 A1 | 11/2004 | Frankowski et al. | |
| 2004/0243229 A1 | 12/2004 | Vidlund et al. | |
| 2004/0267280 A1 | 12/2004 | Nishide et al. | |
| 2005/0038508 A1 | 2/2005 | Gabbay | |
| 2005/0038509 A1 | 2/2005 | Ashe | |
| 2005/0070999 A1 | 3/2005 | Spence | |
| 2005/0075719 A1 | 4/2005 | Bergheim | |
| 2005/0125032 A1 * | 6/2005 | Whisenant | A61B 17/0057 606/213 |
| 2005/0192627 A1 * | 9/2005 | Whisenant | A61B 17/0057 606/213 |
| 2005/0267524 A1 * | 12/2005 | Chanduszko | A61B 17/0057 606/213 |
| 2006/0058871 A1 | 3/2006 | Zakay et al. | |
| 2006/0135966 A1 * | 6/2006 | Schaller | A61B 17/1285 606/139 |
| 2006/0199995 A1 * | 9/2006 | Vijay | A61B 17/12122 600/16 |
| 2006/0201519 A1 | 9/2006 | Frazier et al. | |
| 2006/0241745 A1 | 10/2006 | Solem | |
| 2006/0293739 A1 * | 12/2006 | Vijay | A61B 17/12136 607/122 |
| 2007/0032821 A1 * | 2/2007 | Chin-Chen | A61B 17/0057 606/213 |
| 2007/0093890 A1 | 4/2007 | Eliasen et al. | |
| 2007/0162071 A1 | 7/2007 | Burkett et al. | |
| 2007/0198082 A1 | 8/2007 | Kapadia et al. | |
| 2007/0219627 A1 | 9/2007 | Chu et al. | |
| 2007/0255399 A1 | 11/2007 | Eliasen et al. | |
| 2007/0265700 A1 | 11/2007 | Eliasen et al. | |
| 2007/0270943 A1 | 11/2007 | Solem et al. | |
| 2007/0282429 A1 | 12/2007 | Hauser et al. | |
| 2008/0077180 A1 * | 3/2008 | Kladakis | A61B 17/0057 606/216 |
| 2008/0195126 A1 * | 8/2008 | Solem | A61B 17/0401 606/155 |
| 2008/0243245 A1 | 10/2008 | Thambar et al. | |
| 2009/0048668 A1 | 2/2009 | Wilson et al. | |

(56) References Cited

U.S. PATENT DOCUMENTS

| | | |
|---|---|---|
| 2009/0054723 A1* | 2/2009 | Khairkhahan ..... A61B 17/0057 600/16 |
| 2009/0069885 A1 | 3/2009 | Rahdert et al. |
| 2009/0099596 A1* | 4/2009 | McGuckin, Jr. ............................ A61B 17/12172 606/213 |
| 2009/0137968 A1 | 5/2009 | Rottenberg |
| 2010/0022948 A1 | 1/2010 | Wilson et al. |
| 2010/0023117 A1 | 1/2010 | Yoganathan et al. |
| 2010/0198347 A1 | 8/2010 | Zakay et al. |
| 2010/0298929 A1 | 11/2010 | Thornton et al. |
| 2011/0077733 A1 | 3/2011 | Solem |
| 2011/0098525 A1* | 4/2011 | Kermode ............ A61M 60/468 600/37 |
| 2011/0184512 A1 | 7/2011 | Webler et al. |
| 2011/0224784 A1 | 9/2011 | Quinn |
| 2011/0313515 A1 | 12/2011 | Quadri et al. |
| 2012/0143320 A1 | 6/2012 | Eliasen et al. |
| 2013/0338763 A1 | 12/2013 | Rowe et al. |
| 2014/0277390 A1 | 9/2014 | Ratz et al. |
| 2014/0277427 A1 | 9/2014 | Ratz et al. |
| 2014/0309732 A1 | 10/2014 | Solem |
| 2015/0328000 A1 | 11/2015 | Ratz et al. |
| 2016/0143736 A1 | 5/2016 | Vidlund et al. |
| 2017/0079790 A1* | 3/2017 | Vidlund ............. A61B 17/0401 |
| 2017/0312078 A1 | 11/2017 | Krivoruchko |

FOREIGN PATENT DOCUMENTS

| | | |
|---|---|---|
| WO | 9930647 A1 | 6/1999 |
| WO | 0047139 A1 | 8/2000 |
| WO | 02062236 A1 | 8/2002 |
| WO | 03003949 A2 | 1/2003 |
| WO | 03028558 A2 | 4/2003 |
| WO | 03049619 A2 | 6/2003 |
| WO | 03003949 A3 | 1/2004 |
| WO | 2004012583 A2 | 2/2004 |
| WO | 2004014258 A1 | 2/2004 |
| WO | 2004021893 A1 | 3/2004 |
| WO | 2004030568 A2 | 4/2004 |
| WO | 2004045378 A2 | 6/2004 |
| WO | 2005007036 A1 | 1/2005 |
| WO | 2005027797 A1 | 3/2005 |
| WO | 2005069850 A2 | 8/2005 |
| WO | 2006032051 A2 | 3/2006 |
| WO | 2006049629 A1 | 5/2006 |
| WO | 2006111391 A1 | 10/2006 |
| WO | 2006127509 A2 | 11/2006 |
| WO | 2007050256 A2 | 5/2007 |
| WO | 2011097355 A2 | 8/2011 |
| WO | 2015012122 A1 | 1/2015 |

* cited by examiner

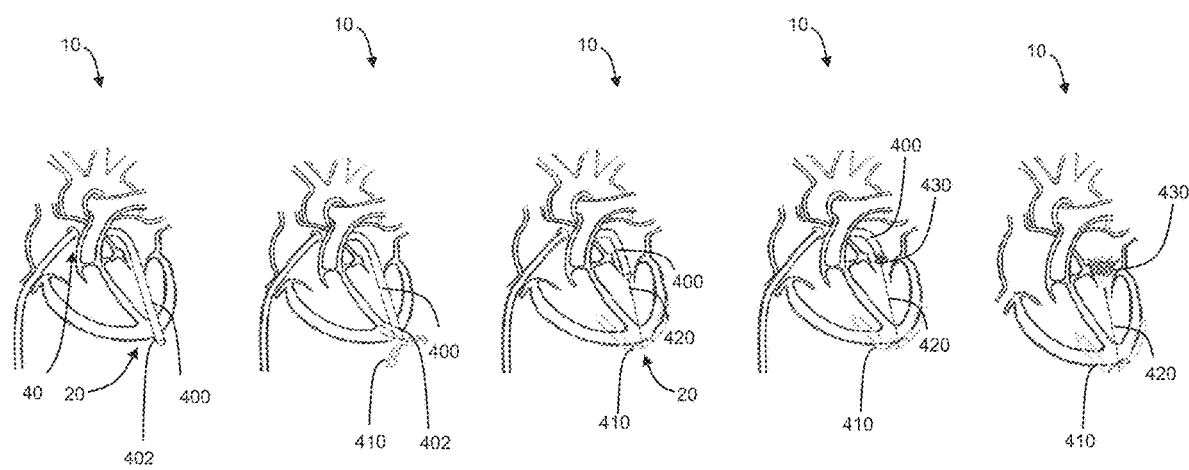

HEART SHAPE PRESERVING ANCHOR

RELATED APPLICATIONS

This application is a continuation of International Application No. PCT/US2019/014554, filed Jan. 22, 2019, which designates the United States and was published in English by the International Bureau on Jul. 25, 2019 as WO 2019/144121, which claims the benefit of U.S. Provisional Application No. 62/620,367, filed Jan. 22, 2018.

BACKGROUND

Field

Certain embodiments disclosed herein relate generally to valve prostheses. In particular, certain embodiments relate to an anchoring system for use with replacement heart valves, such as for the mitral valve, wherein the anchoring system is configured to preserve the natural shape of the heart.

Background

Human heart valves, which include the aortic, pulmonary, mitral and tricuspid valves, function essentially as one-way valves operating in synchronization with the pumping heart. The valves allow blood to flow downstream, but block blood from flowing upstream. Diseased heart valves exhibit impairments such as narrowing of the valve or regurgitation, which inhibit the valves' ability to control blood flow. Such impairments reduce the heart's blood-pumping efficiency and can be a debilitating and life threatening condition. For example, valve insufficiency can lead to conditions such as heart hypertrophy and dilation of the ventricle. Thus, extensive efforts have been made to develop methods and apparatuses to repair or replace impaired heart valves.

Prostheses exist to correct problems associated with impaired heart valves. For example, mechanical and tissue-based heart valve prostheses can be used to replace impaired native heart valves. More recently, substantial effort has been dedicated to developing replacement heart valves, particularly tissue-based replacement heart valves that can be delivered with less trauma to the patient than through open heart surgery. Replacement valves are being designed to be delivered through minimally invasive procedures and even percutaneous procedures. Such replacement valves often include a tissue-based valve body that is connected to an expandable frame that is then delivered to the native valve's annulus.

These replacement valves are often intended to at least partially block blood flow. However, a problem occurs when blood flows around the valve on the outside of the prosthesis. An additional challenge relates to the ability of such prostheses to be secured relative to intralumenal tissue, e.g., tissue within any body lumen or cavity, in an atraumatic manner.

SUMMARY

Embodiments of the present disclosure are directed to an anchoring system for a prosthesis, such as but not limited to a replacement heart valve. In some embodiments, an anchor for a replacement heart valve prosthesis can include a frame and a tether for attachment to a replacement heart valve prosthesis. The frame can have one or more wings extending upwardly from a lower end. The frame can have a generally conical shape to generally conform to the shape of the heart.

In some embodiments, a chordal replacement system can include a frame and a tether for attachment to a leaflet of a native mitral valve. The frame can have one or more wings extending upwardly from a lower end. The frame can have a generally conical shape to generally conform to the shape of the heart.

In some embodiments, a method of performing a procedure at a patient's heart can include delivering an anchor frame to an apex of the heart. The anchor frame can have one or more wings extending upwardly from a lower end. The frame can have a generally conical shape. The method can further include expanding the anchor frame, seating the lower end of the anchor frame against the apex of the heart, and applying tension to a tether connecting the anchor frame to a location within a chamber of the patient's heart, such as a replacement heart valve within a chamber of the patient's heart or native leaflets within a chamber of the patient's heart.

BRIEF DESCRIPTION OF THE DRAWINGS

These and other features, aspects and advantages are described below with reference to the drawings, which are intended to illustrate embodiments of prostheses including embodiments of various components of these prostheses.

FIGS. 5A-5E are a schematic representation of transseptal deployment of an embodiment of a prosthesis having an anchoring system.

DETAILED DESCRIPTION

Figure 1:
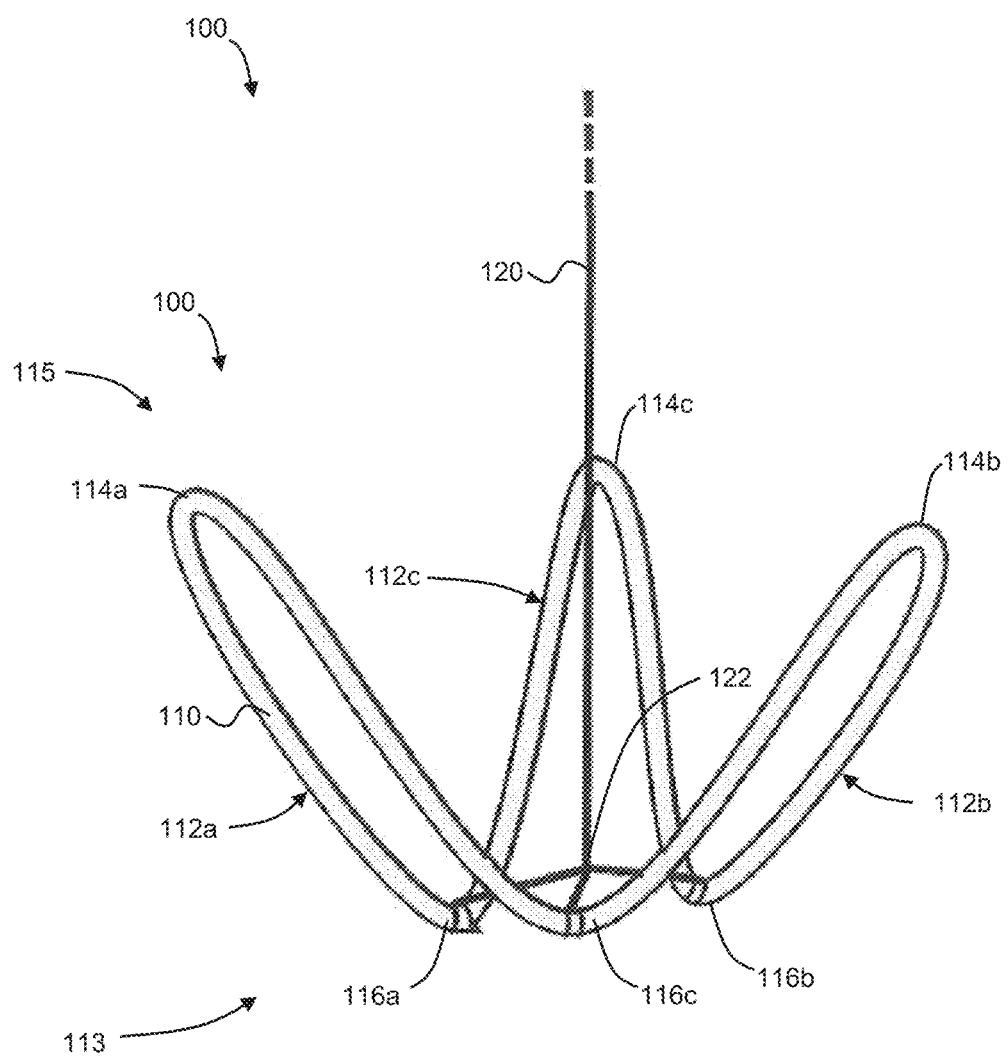
FIG. 1 is a side view of an embodiment of an anchoring system for a prosthesis.

The present specification and drawings provide aspects and features of the disclosure in the context of several embodiments of anchoring systems, prostheses, replacement heart valves, and methods that are configured for use in the vasculature of a patient, such as for replacement of natural heart valves in a patient. These embodiments may be discussed in connection with replacing specific valves such as the patient's mitral valve. However, it is to be understood that the features and concepts discussed herein can be applied to replacing other types of valves including, but not limited to, the aortic valve, the pulmonary valve, and the tricuspid valve. Moreover, it is to be understood that the features and concepts discussed herein can be applied to products other than heart valve implants. For example, the controlled positioning, deployment, and/or securing features described herein can be applied to medical implants, for example other types of expandable prostheses, for use elsewhere in the body, such as within a vein, or the like. In addition, particular features of a prosthesis should not be taken as limiting, and features of any one embodiment discussed herein can be combined with features of other embodiments as desired and when appropriate.

Certain terminology may be used in the following description for the purpose of reference only, and thus are not intended to be limiting. For example, terms such as "upper", "lower", "upward", "downward", "above", "below", "top", "bottom" and similar terms refer to directions in the drawings to which reference is made. Terms such as "proximal", "distal", "radially outward", "radially inward", "outer", "inner", and "side", describe the orientation and/or location of portions of the components or elements within a consistent but arbitrary frame of reference, which is made clear by reference to the text and the associated drawings describing the components or elements under discussion. Such terminology may include the words specifically mentioned above, derivatives thereof, and words of similar import. Similarly, the terms "first", "second", and other such numerical terms referring to structures neither imply a sequence or order unless clearly indicated by the context.

In some embodiments, the term "proximal" may refer to the parts of the prostheses, or components thereof, which are located closer to the operator of the device and system (e.g., the clinician implanting the prosthesis). The term "distal" may refer to the parts of the prostheses, or components thereof, which are located further from the operator of the device and system (e.g., the clinician implanting the prosthesis). However, it is to be understood that this terminology may be reversed depending on the delivery technique utilized (e.g., a transapical approach as compared to a transseptal approach).

Figure 2:
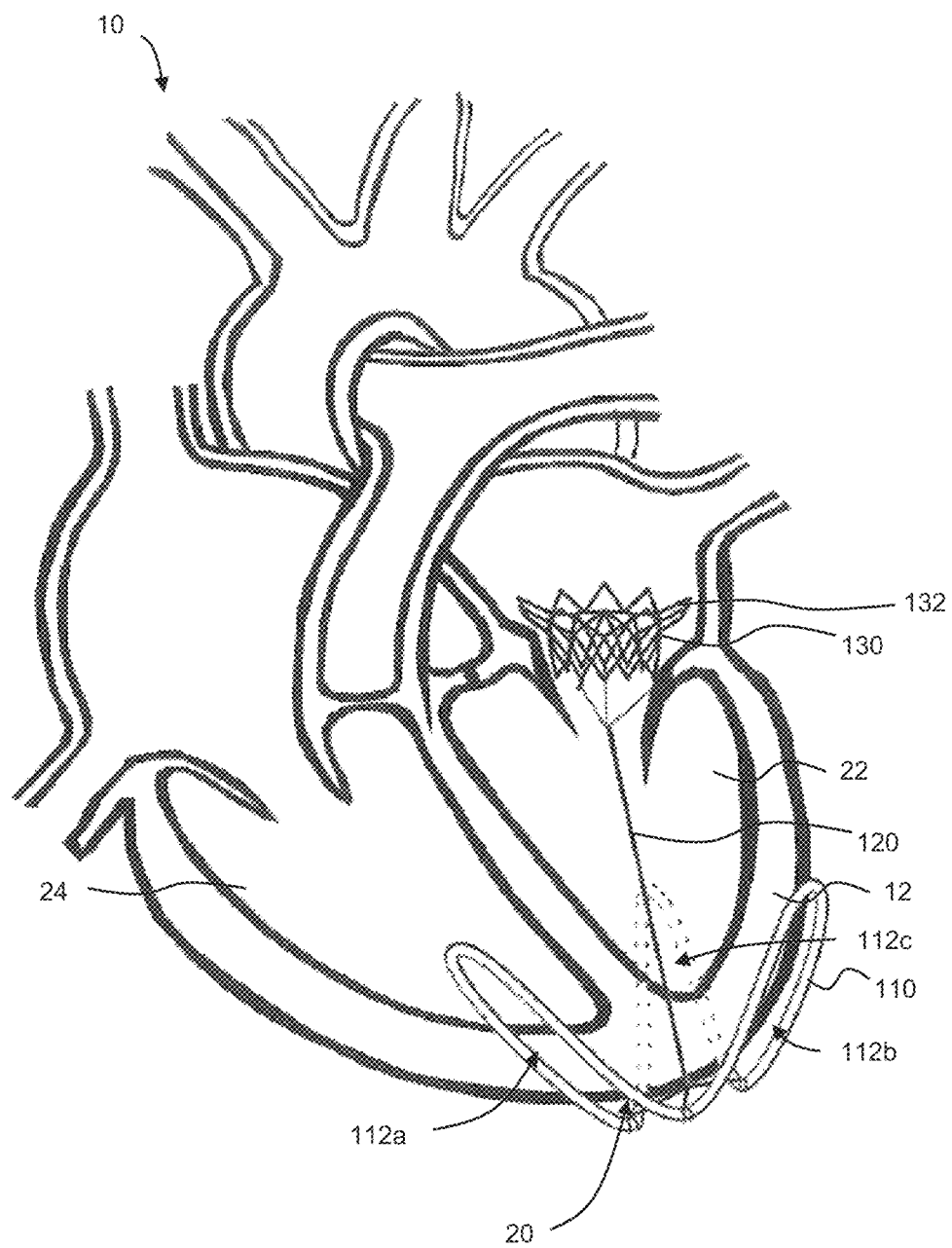
FIG. 2 is a schematic of the anchoring system of FIG. 1 anchoring a prosthesis to the native mitral valve.

With reference first to FIGS. 1 and 2, an embodiment of an anchoring system 100 in an expanded configuration is illustrated. As shown in the illustrated embodiment, the anchoring system 100 can have frame 110 shaped to generally match the shape of the heart 10. For example, in some embodiments, the frame 110 can have a body with a generally conical shape to match the shape of the heart around the apex 20 of the left ventricle 22 of the heart 10 and/or the apex of the right ventricle 24. The frame 110 can include three wings or fingers 112a-c that extend upwardly from a lower end 113 of the frame 110 towards an upper end 115 of the frame 110. The wings or fingers 112a-c can form an angle with the tether 120. For example, the wings or fingers 112a-c can form an angle between about 20 degrees to about 90 degrees, between about 30 degrees to about 90 degrees, between about 40 degrees to about 90 degrees, any sub-range within these ranges, or other angles as desired. In some embodiments, the wings or fingers 112a-c can bend inwardly towards the tether 120. Although the frame 110 is shown with three wings or fingers 112a-c, it is to be understood that the frame 110 can have fewer or greater than three wings or fingers 112a-c. Moreover, although the wings or fingers 112a-c are shown equally spaced apart from each other, it is to be understood that the spacing between one or more of the wings or fingers 112a-c can differ. For example, the spacing between wings or fingers 112a-b can be less than the spacing between wings or fingers 112a and 112c.

As shown in the illustrated embodiment, the frame 110 can have a wireform shape bent to have one or more upper apices 114a-c and one or more lower apices 116a-c. The wireform shape of the frame 110 can advantageously allow the frame 110 to collapse into a small diameter during delivery to a target anchoring site. Moreover, the wireform shape of the frame 110 can allow parts of the frame 110 to deform without significantly affecting other parts of the frame 110. The wireform can be manufactured from metals such as nitinol or stainless steel, polymers such as polytetrafluoroethylene (PTFE), and/or other biocompatible materials. The wireform can include a covering (not shown) such as a soft biocompatible material, including but not limited to a fabric or polymer.

As shown in FIG. 2, the lower apices 116a-c of the frame 110 can be positioned at or proximate the apex 20 of the heart 10 and the frame 110. The wings or fingers 112a-c can extend upwardly and engage portions of the heart wall 12. In some embodiments, the frame 110 can extend along at least 10% the length of the heart, at least about 20% the length of the heart, at least about 30% the length of the heart, at least about 40% the length of the heart, or other lengths as desired. In some embodiments, the frame 110 can have a longitudinal length of at least about 4 cm, at least about 6 cm, at least about 8 cm, or other lengths as desired. The wings or fingers 112a-c can have a length of between about 2 cm to 10 cm, between about 4 cm to 8 cm, about 4 cm, any sub-ranges within these ranges, or other lengths as desired. Although the wings or fingers 112a-c are shown as having similar lengths, it is to be understood that one or more of the wings or fingers 112a-c can have different lengths.

The size, shape, and/or construction of the frame 110 helps ensure that the frame 110 distributes anchoring forces over a relatively large area on the heart 10, thereby reducing pressures applied to the heart 10. In some embodiments, the frame 110 can distribute anchoring forces along non-apical portions of the heart 10 in lieu of, or in addition to, anchoring forces along the apex 20 of the heart 10. This reduces the likelihood that the natural, conical shape of the heart 10 is deformed into a shape with reduced pumping performance. For example, the distribution of loads along non-apical portions of the heart 10 can reduce the likelihood that the apex is pulled inwardly, which can flatten the bottom of the ventricle. In some embodiments, the frame 110 can be deformable to better conform to the shape of the heart 10. As noted above, the frame 110 can be formed from a flexible wireform and/or covering, which can allow the frame 110 to better conform to the shape of the heart 10. This can be particularly advantageous since the heart 10 dynamically alters its shape throughout the cardiac cycle (e.g., diastole and systole). The deformable characteristic of the frame 110 can allow the frame 110 to maintain a substantial contact area with the heart 10 throughout these various phases. Moreover, the wire structure of the frame 110 and individual wings 112a-c can allow parts of the frame 110 to deform without substantially affecting other parts of the frame 110. This can enhance conformance of the frame 110 with the heart 10.

As shown in FIG. 2, the tether 120 is attached at one end to the frame 110 and at the other end to a prosthesis 130. The prosthesis 130 can include a flange 132 sized to contact an atrial surface of the native mitral valve. It is to be understood that prosthesis 130, and any other prosthesis described herein, may include features and concepts similar to those disclosed in U.S. Pat. Nos. 8,403,983, 8,414,644, 8,652,203, 9,681,951 and U.S. Publication Nos. 2011/0313515, 2014/0277390, 2014/0277427, and 2015/0328000, the entireties of each of which are hereby incorporated by reference and made a part of this specification. The lower end of the tether 120 is attached to each of the lower apices 116a-c and extends from a junction 122, which can be positioned along a longitudinal axis of the anchoring system 100. Due to the reduced likelihood that the natural, conical shape of the heart is deformed over time, the amount of tension applied by the tether to the prosthesis 130 can remain generally constant. This beneficially reduces the likelihood that the prosthesis 130 loosens over time.

Figure 3:
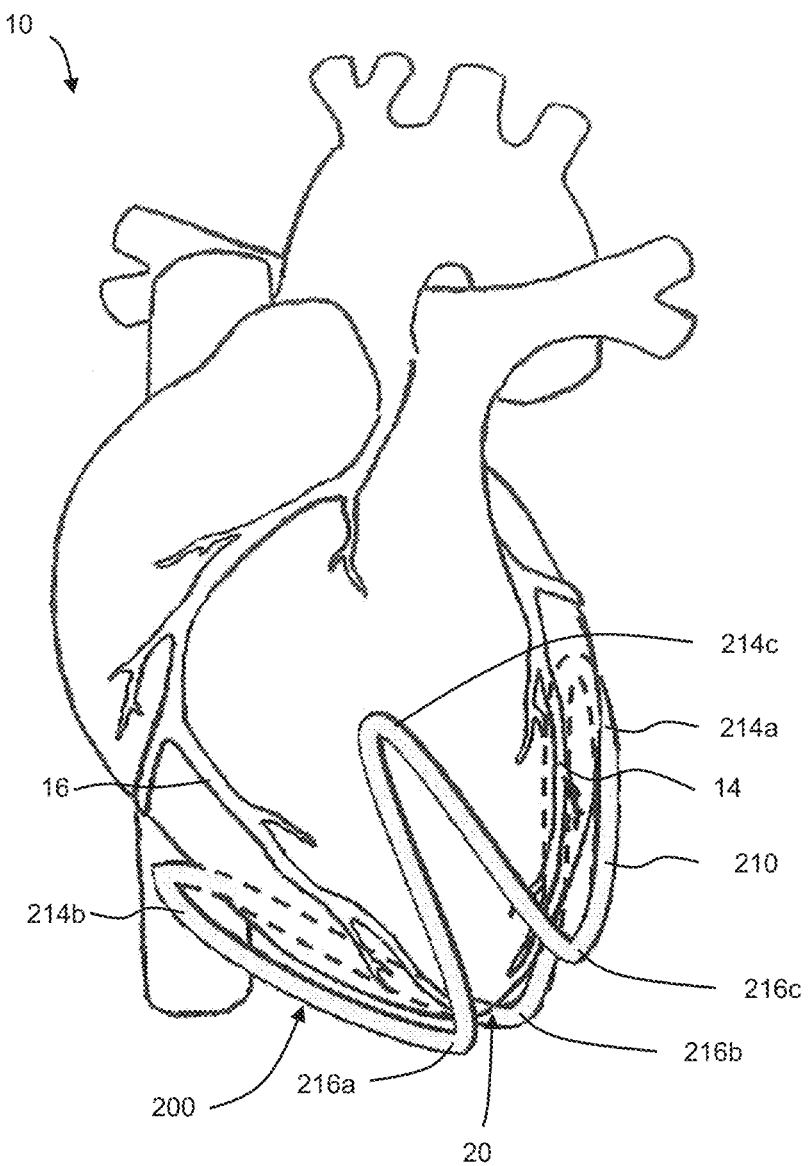
FIG. 3 side view of an embodiment of an anchoring system attached to an exterior of a heart.

With reference next to FIG. 3, an embodiment of an anchoring system 200 is illustrated. The shape and geometry of the anchoring system 200 can be similar to that of anchoring system 100 albeit enlarged. For example, the lower apices 216a-c of frame 210 can be positioned at or proximate an apex 20 of the heart 10. In some implementations, the first upper apex 214a can be positioned between the left anterior descending artery (LAD) 14 and the acute marginal artery (not shown) on the left anterolateral side of the left ventricle. The second upper apex 214b can be positioned between the acute marginal artery (not shown) and the posterior descending artery (not shown) on the posterolateral side of the left ventricle. The third upper apex 214c can be positioned on the right lateral side of the right ventricle, anterior or posterior to the obtuse marginal 16. As shown, the frame 210 significantly or wholly avoids contacting the coronary arteries, which can beneficially maintain blood flow through these arteries. Positioning of the anchor in this orientation can be performed using direct vision, fluoroscopy, or any other visualization mechanism. In some embodiments, the shape and/or spacing of the wings or fingers of frame 210 can be further tailored based on the patient's anatomy.

Figures 4A, 4B, 4C, 4D, 4E:
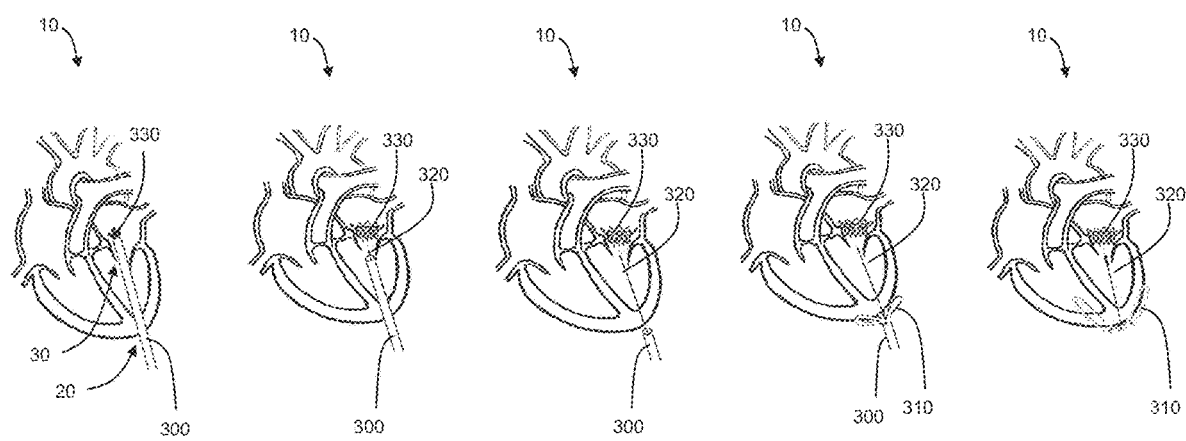
FIGS. 4A-4E are a schematic representation of transapical deployment of an embodiment of a prosthesis having an anchoring system.

With reference next to FIGS. 4A-4E, an embodiment of a transapical delivery method is illustrated. While the method is described in connection with a native mitral valve, it is to be understood that the procedure can be utilized for other native heart valves, such as a tricuspid valve. As shown in FIG. 4A, a delivery instrument 300 can be advanced through an apex 20 of the heart 10 to the native mitral valve 30. A portion of the delivery instrument 300, such as a catheter or sheath, can be moved relative to the prosthesis 330 to expose the prosthesis 330 and allow the prosthesis 330 to partially expand. For example, the catheter or sheath can be retracted relative to the prosthesis 330. As shown in FIG. 4B, the catheter or sheath can be further moved relative to the prosthesis 330 to further expand the prosthesis. The prosthesis 330 can be pulled proximally to seat the prosthesis 330 against a portion of the native mitral valve, such as an atrial surface of the annulus. This can be performed by pulling on suture or tether 320. As shown in FIG. 4C, the sheath can be further moved relative to the prosthesis 330 such that a distal end of the catheter or sheath is positioned outside of the heart. As shown in FIG. 4D, the anchor frame 310 can be advanced through the catheter or sheath towards the heart 10. The anchor frame 310 can begin to expand as it extends beyond the sheath or catheter. As shown in FIG. 4E, the anchor frame 310 can be fully advanced through the catheter or sheath to deploy the anchor frame 310 against tissue of the heart 10. The anchor frame 310 can be seated against or proximate the apex 20 of the heart 10. In some embodiments, the length of the tether 320 can be modified at this stage, or any preceding stage, to apply a desired amount of tension to the prosthesis 330.

With reference next to FIGS. 5A-5E, an embodiment of a transseptal delivery method is illustrated. While the method is described in connection with a native mitral valve, it is to be understood that the procedure can be utilized for other native heart valves, such as a tricuspid valve. As shown in FIG. 5A, a delivery instrument 400 can be advanced through a femoral vein of a patient and into the left ventricle via an opening in the septum 40. As shown, a distal end 402 of the delivery instrument 400 can pass through an opening in the apex 20. As shown in FIG. 5B, relative movement between an anchor frame 410 and a portion of the delivery instrument 400, such as a catheter or sheath, can expose the anchor frame 410. For example, the anchor frame 410 can be advanced through the catheter or sheath and advanced outside of the distal end 402. As shown in FIG. 5C, further movement between the anchor frame 410 and the catheter or sheath can deploy the anchor frame 410. The anchor frame 410 can be pulled proximally to seat the anchor frame 410 against or proximate the apex 20 of the heart 10. This can be performed by pulling on suture or tether 420. As shown in FIG. 5D, the catheter or sheath can be moved relative to the prosthesis 430 to expose the prosthesis 430 and allow the prosthesis 430 to partially expand. For example, the catheter or sheath can be retracted relative to the prosthesis 430. As shown in FIG. 5E, the catheter or sheath can be further moved relative to the prosthesis 430 to further expand the prosthesis 430. In some embodiments, the length of the tether 420 can be modified at this stage, or any preceding stage, to apply a desired amount of tension to the prosthesis 430.

Figure 6:
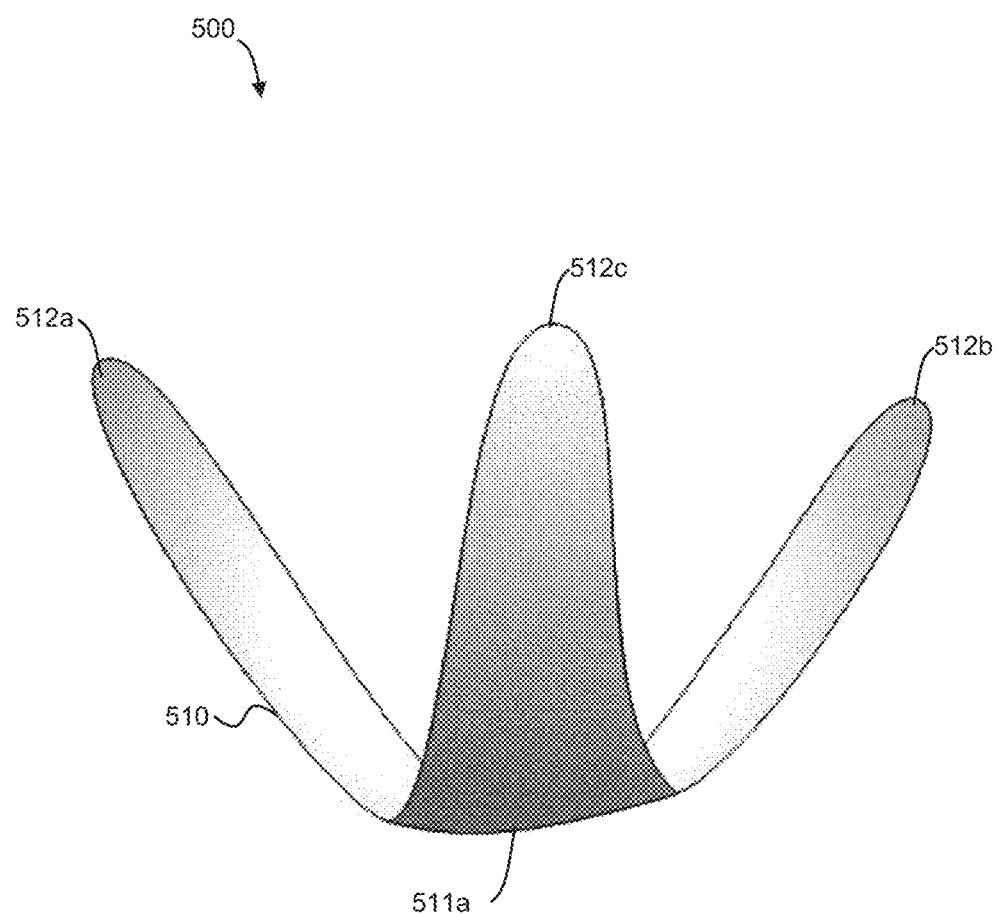
FIG. 6 is a side view of another embodiment of an anchoring system for a prosthesis.

With reference next to FIG. 6, another embodiment of an anchoring system 500 in an expanded configuration is illustrated. As shown in the illustrated embodiment, the anchoring system 500 can have frame 510 shaped to generally match the shape of the heart. For example, in some embodiments, the frame 510 can have a body generally conical shape to match the apex of the heart. The frame 510 can be formed from a sheet and shaped to have one or more wings or fingers 512a-c extending from a base 511a. The sheet can be manufactured from metals such as nitinol or stainless steel, polymers such as polytetrafluoroethylene (PTFE), and/or other biocompatible materials. The wings or fingers 512a-c of frame 510 can allow parts of the frame 510 to deform without significantly affecting other parts of the frame 510. For example, deformation of wing or finger 512a can have little effect on the shape of wing or finger 512b. Moreover, the spacing between wings or fingers 512a-c can allow the frame 510 to be positioned to avoid parts of the native anatomy, such as coronary arteries.

In some embodiments, the frame 510 can include a covering, such as a soft biocompatible material, including but not limited to a fabric or polymer. The large surface area of the frame 510 can help ensure that the frame 510 distributes anchoring forces over a relatively large area on the heart, thereby reducing pressures applied to the heart. A tether (not shown) can extend from the base 511a.

Figure 7:
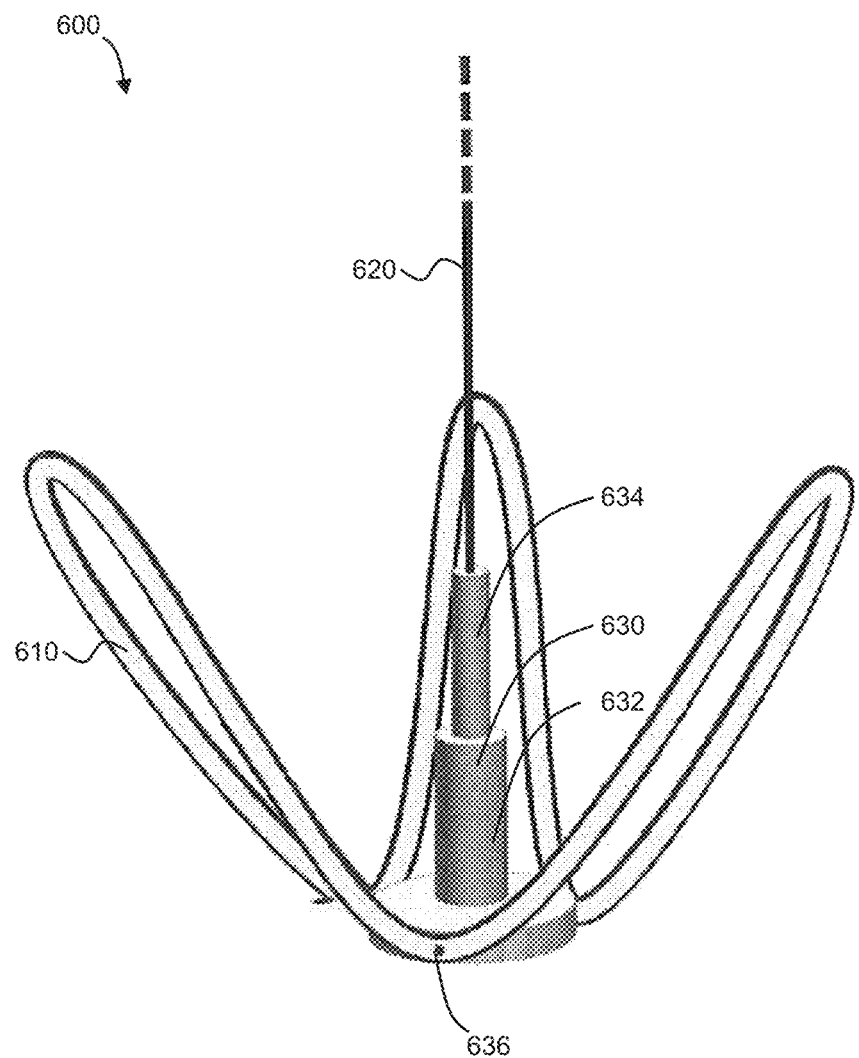
FIG. 7 is a side view of another embodiment of an anchoring system for a prosthesis, the anchoring system having an adjustment system.

With reference next to FIGS. 7-10, another embodiment of an anchoring system 600 in an expanded configuration is illustrated. With reference first to FIG. 7, the anchoring system 600 can include an anchor frame 610 similar to that described in connection with FIGS. 1 and 2; however, it is to be understood that the anchor frame 610 can include similar features and/or structures to frames 200, 510. The anchoring system 600 can include a tether 620 and a tether adjustment mechanism 630. As shown, the tether adjustment mechanism 630 can include a housing 632 and a piston 634 that can be moved relative to the housing. The housing 632 can be attached to lower apices of the frame 610 via one or more fasteners 636 including, but not limited to, mechanical and/or adhesive fasteners. The piston 634 can be attached to the tether 632. Relative movement between the piston 634 and the housing 632 can adjust the distance between tether 620 and the frame 610. This can beneficially allow a surgeon to adjust tension in the tether 620. In embodiments where the tether adjustment mechanism 630 is remotely operated, this can allow a surgeon to adjust tension without surgically accessing the anchor 610 and tether 620. This can advantageously allow the surgeon to adjust tension in the tether 620 days, months, or years after the surgical operation. This can be particularly beneficial in instances where tension on the tether 620 decreases over time. For example, the shape of the heart may gradually change leading to a reduced distance between a prosthesis (not shown) and the anchor 610, the prosthesis may seat differently, or the tether may stretch.

Figure 8:
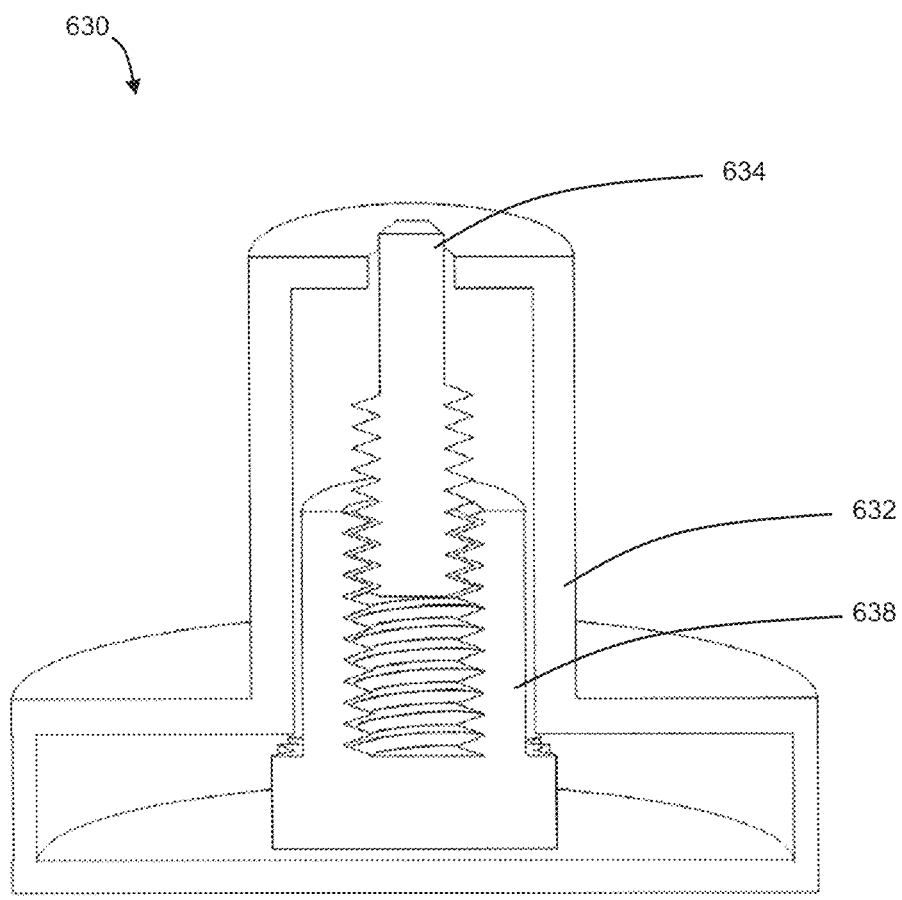
FIG. 8 is a schematic, side-oriented cross-section of the adjustment system of FIG. 7.
Figure 9:
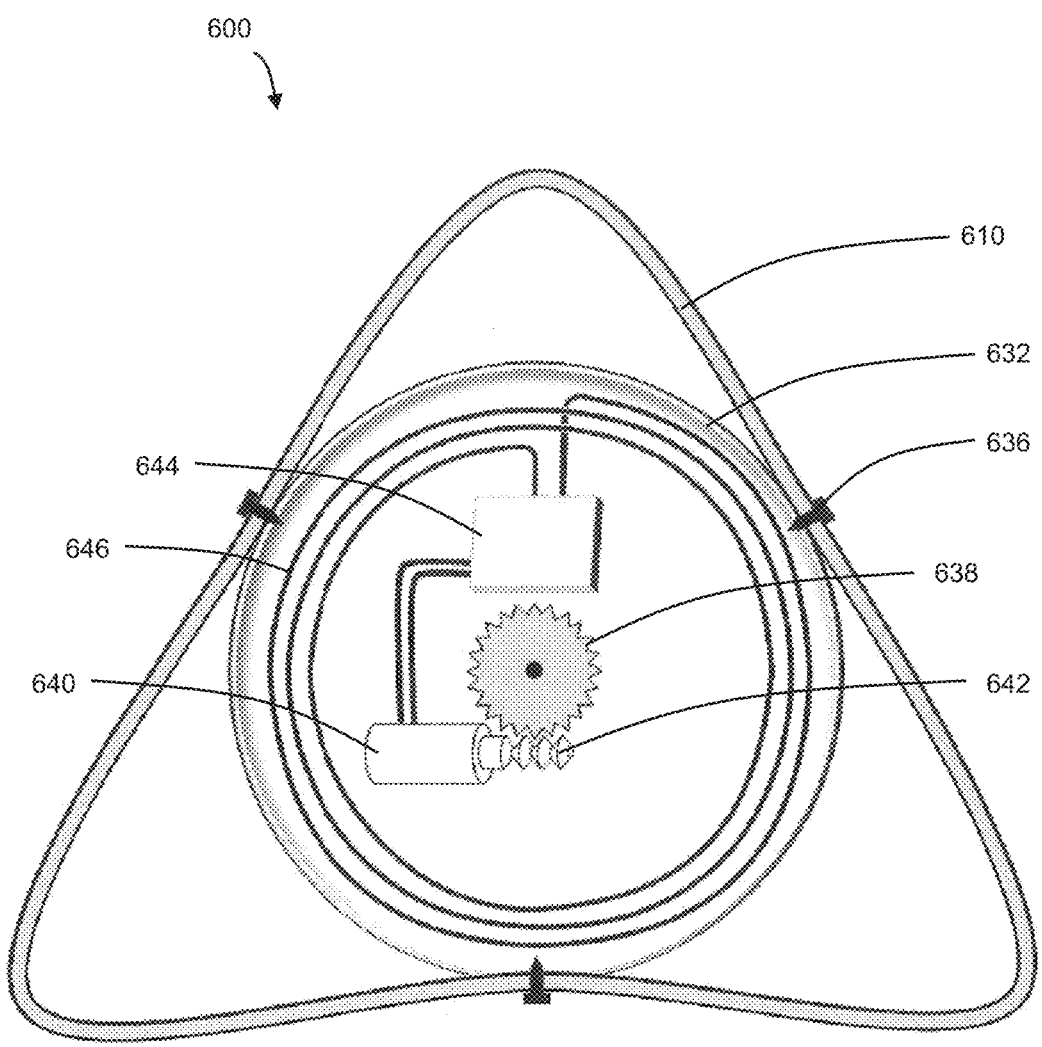
FIG. 9 is a schematic, top-oriented cross-section of the adjustment system of FIG. 7.

With reference next to FIGS. 8 and 9, schematic cross-sections of the tether adjustment mechanism 630 are illustrated. As shown in the illustrated embodiment, the height of the piston 634 can be adjusted via rotation of a screw drive 638. The screw drive 638 can be operated via a motor 640 having a worm gear 642. The tether adjustment mechanism 630 can include an electronic module 644 for operating the motor 640. The electronic module 644 can include a controller for converting drive commands to drive signals to the motor 640 and/or regulate power provided to the motor 640. The electronic module 644 can also include a wireless receiver to receive wireless signals, which can beneficially allow the tether adjustment mechanism to be remotely controlled. The tether adjustment mechanism 644 can include one or more antennas 646 to receive wireless signals. A unique passcode or security code can be implemented within the electronics module 644 to reduce the likelihood that the motor is driven by random electromagnetic fields rather than a signal provided by the surgeon. The unique passcode or security code can be included on a remote control device (648 in FIG. 10).

In some embodiments, the tether adjustment mechanism 630 can be wirelessly powered. For example, the tether adjustment mechanism 630 can allow for inductive power transfer. In some embodiments, a battery can be omitted thereby extending the usable lifespan of the tether adjustment mechanism 630; however, it is to be understood that a battery can be used in combination with, or in lieu of, inductive power transfer. Power can be transmitted inductively to the tether adjustment mechanism 630 via one or more antennas 646.

Figure 10:
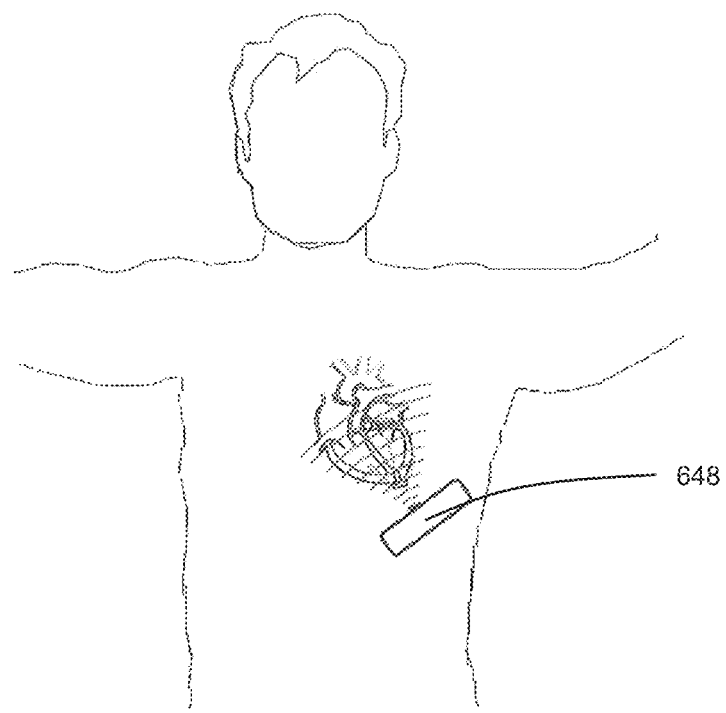
FIG. 10 is a schematic of a method of adjusting the adjustment system of FIG. 7.

As shown in FIG. 10, the tether adjustment mechanism 630 can be wirelessly controlled with a remote control device 648. The surgeon can perform this operation under ultrasound echocardiography, or other visualization techniques, to ensure that the tether is being adjusted in an appropriate manner. In some embodiments, the wireless range between the tether adjustment mechanism 630 and the remote control device 648 can be relatively short in order to further reduce the likelihood of operation by random electromagnetic fields. For example, the wireless range can be less than 20 cm, less than 15 cm, less than 10 cm, or other wireless ranges as desired. However, it is to be understood that longer ranges can also be utilized.

Figure 11:
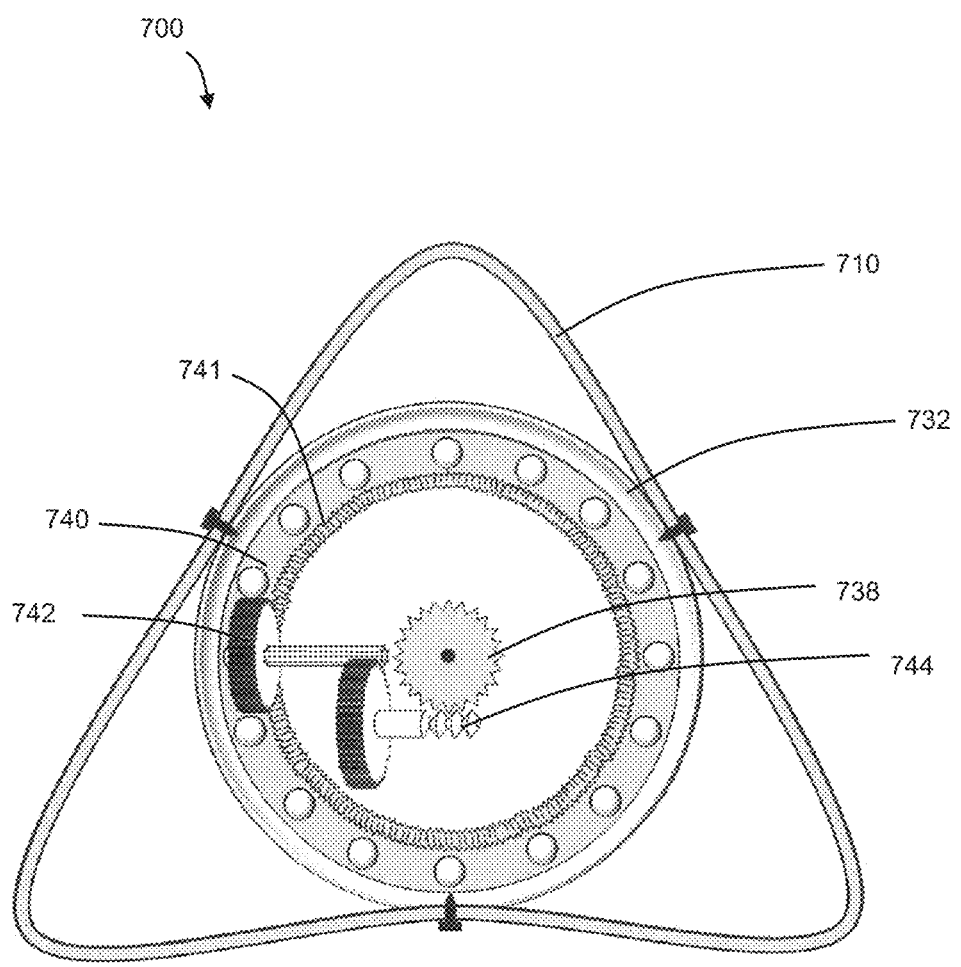
FIG. 11 is a schematic, top-oriented cross-section of another embodiment of an adjustment system.

With reference next to FIG. 11, another embodiment of an anchoring system 700 in an expanded configuration is illustrated. The anchoring system 700 can include an anchor frame 710 similar to that described in connection with FIGS. 1 and 2; however, it is to be understood that the anchor frame 710 can include similar features and/or structures to anchor frame 710. The anchoring system 700 can include a tether adjustment mechanism 730 with features similar to those of tether adjustment mechanism 630, such as a housing 732, piston (not shown), which can be attached to a tether (not shown), and a screw drive 738 for adjusting the height of the piston.

As shown in the illustrated embodiment, the tether adjustment mechanism 730 can be driven via an external magnetic field. A magnetic wheel 740 can be operated via a magnetic force supplied externally. For example, a remote controller can create a rotating magnetic field to rotate the wheel 740. The wheel 740 can include teeth 741 that engage complementary teeth of a sprocket or gear 742. The sprocket or gear 742 can rotatably drive a second sprocket or gear 744 having a worm gear. The worm gear can rotate the screw drive 738 to adjust the height of the piston. Use of a magnetically driven motor can beneficially reduce the amount of electronics contained within the tether adjustment mechanism. Although two sprockets 742, 744 are shown, the number of sprockets can be varied as desired.

Figure 12:
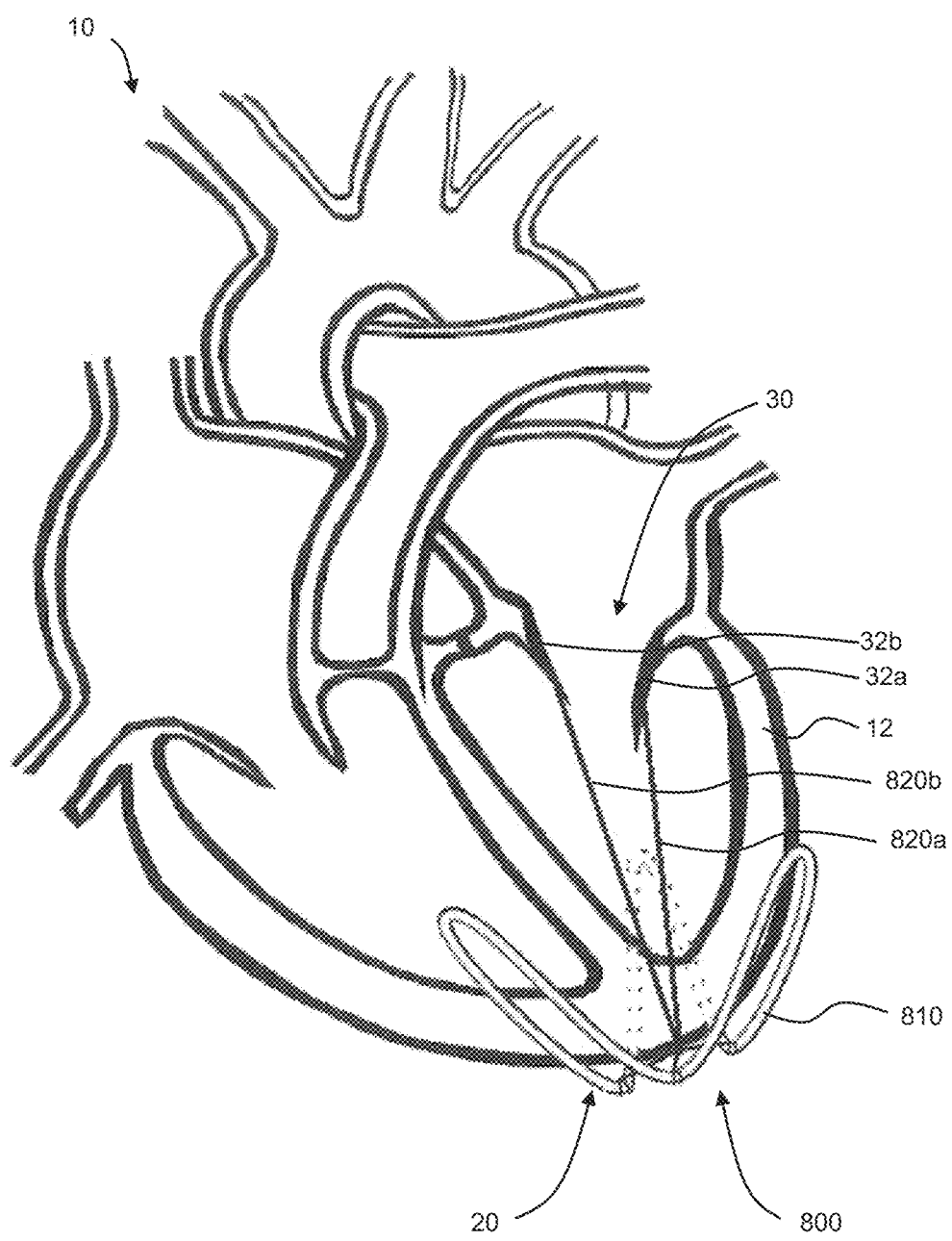
FIG. 12 is a schematic of an embodiment of a chordal replacement system.

With reference next to FIG. 12, an embodiment of a chordal replacement system 800 in an expanded configuration is illustrated. The system 800 can be used to support chordal replacement of a native valve, such as the native mitral valve 30. As shown in the illustrated embodiment, the system 800 can have frame 810 shaped to generally match the shape of the heart. For example, in some embodiments, the frame 810 can have the same features and/or characteristics of other frames described herein including, but not limited to, frame 110. The system 800 can include one or more tethers 820a, 820b that are tethered to mitral valve leaflets 32a, 32b. As such, the tethers 820a, 820b can function as a chordal replacement for the native mitral valve 30.

Figure 13:
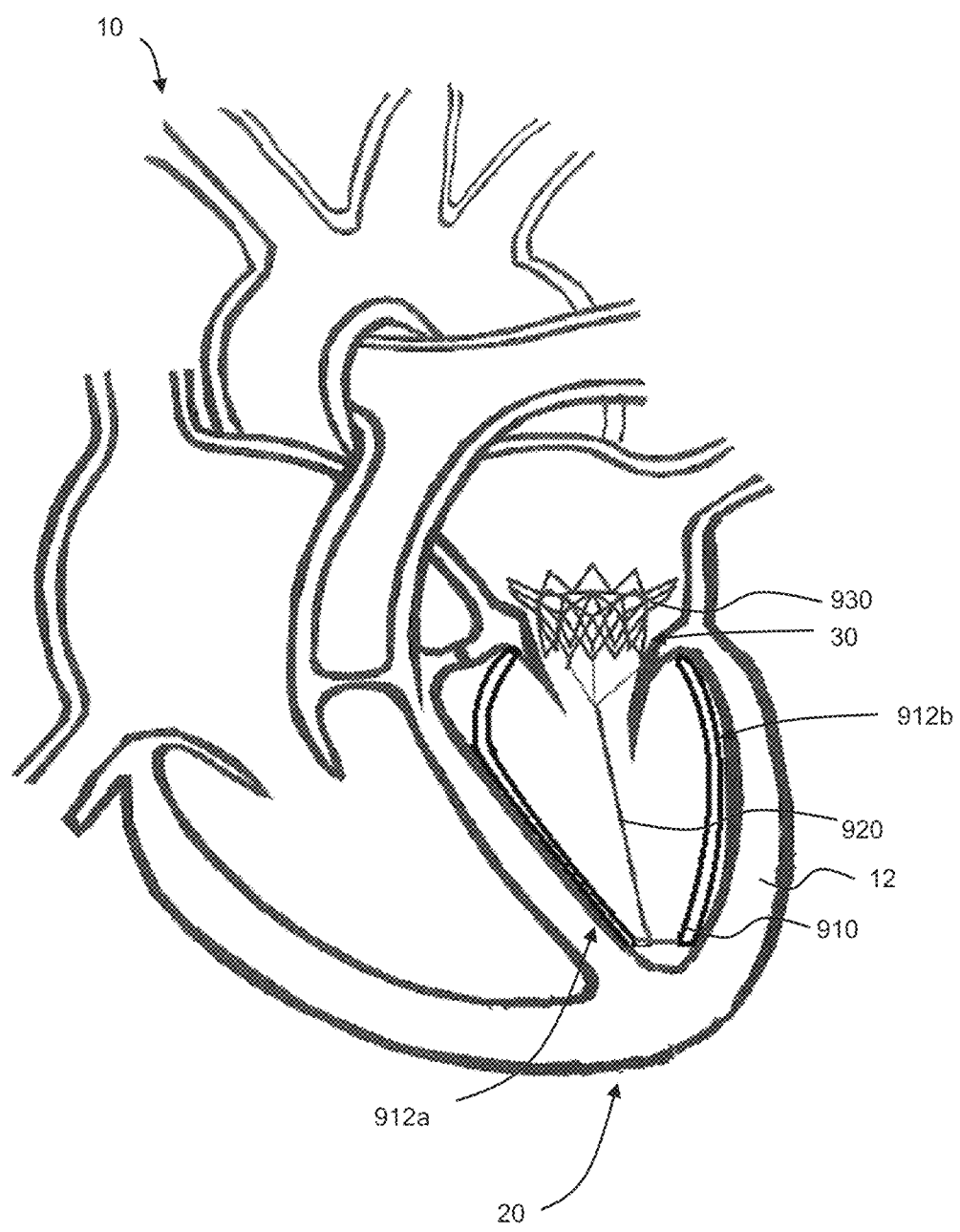
FIG. 13 is a schematic of another embodiment of an anchoring system anchoring a prosthesis to the native mitral valve.
Figure 14:
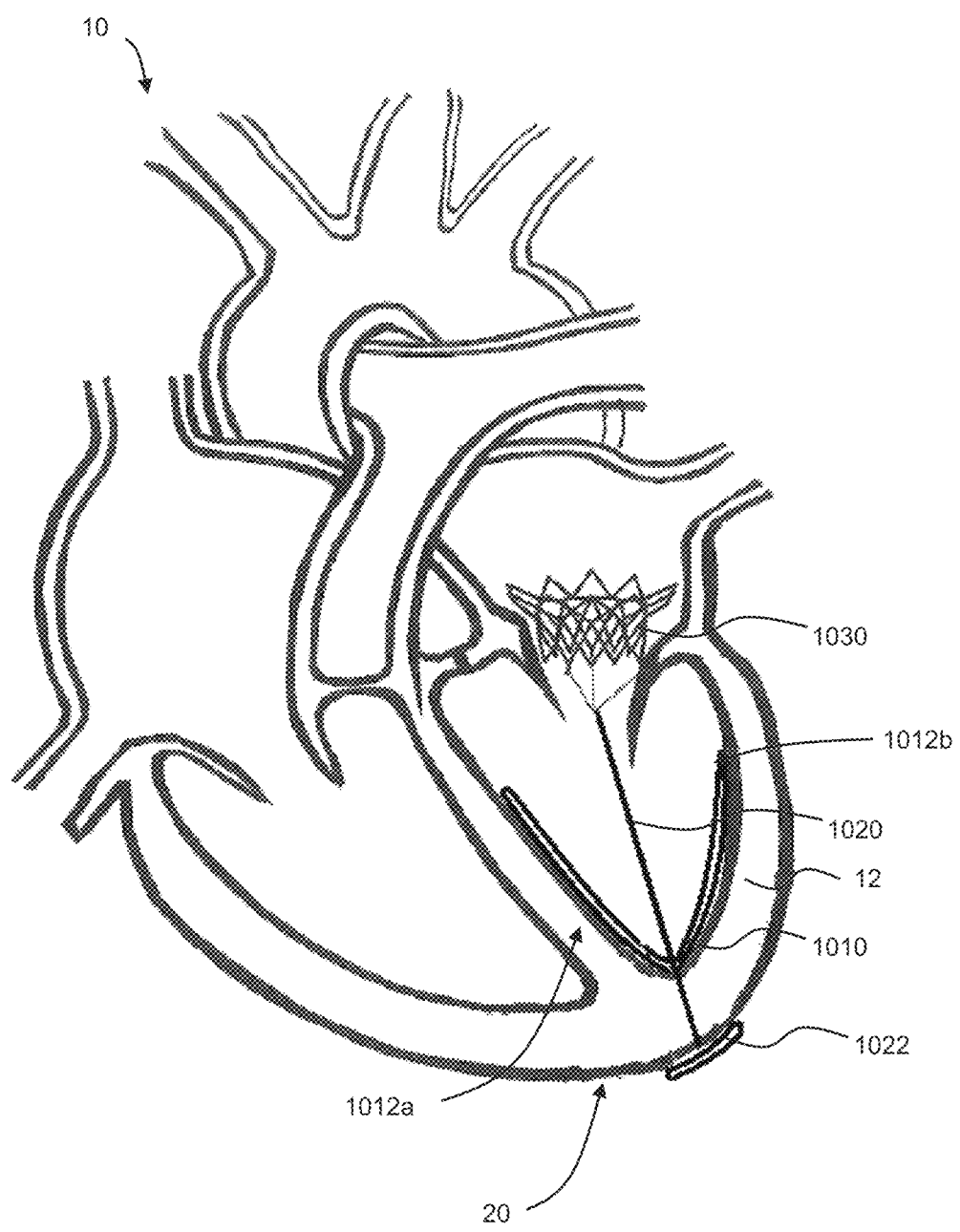
FIG. 14 is a schematic of another embodiment of an anchoring system anchoring a prosthesis to the native mitral valve.

With reference next to FIGS. 13 and 14, in some embodiments the frame of the anchor can be positioned within the ventricle rather than outside the ventricle. With reference first to FIG. 13, a frame 910 of an anchoring system can be positioned within the left ventricle. The frame 910 can include one or more wings or fingers 912a, 912b extending upwardly. As shown, the tips of the wings or fingers 912a, 912b can engage a surface of the ventricle, such as a ventricular surface of the native mitral valve 30. The shape of the frame 910, along with contact along the tips of the wings or fingers 912a, 912b can inhibit movement of the frame 910 within the ventricle. In some embodiments, the frame 910 can be secured within the ventricle via engagement with other portions of the heart, such as chordae tendineae. A tether 920 can couple the frame 910 to a prosthesis 930.

With reference next to FIG. 14, a frame 1010 of an anchoring system can be positioned within the left ventricle. The frame 1010 can include one or more wings or fingers 1012a, 1012b extending upwardly. As shown, the tips of the wings or fingers 1012a, 1012b can extend a partial extent of the heart wall 12. The frame 1010 can be retained in position via an anchoring element 1022 that engages an exterior surface of the heart 10. The anchoring element 1022 can be coupled to the frame 1010 via a tether 1020 thereby inhibiting movement of the frame 1010 in a direction towards the left atrium. The same tether 1020 can couple the frame 1010 and the anchoring element 1022 to a prosthesis 1030. In other embodiments, a separate tether (not shown) can be used to couple the frame 1010 to the anchoring element 1022.

While the embodiments of anchoring systems described above can be maintained on the patient's heart permanently, or at least while the replacement valve remains in position, it is to be understood that components of the anchoring system, such as the frame or tether, can be temporary. In some embodiments, the frame and/or tether can be removed from the heart after the replacement valve is securely maintained in the native valve. For example, the replacement valve can be designed to allow tissue ingrowth to further secure the replacement valve to the native valve. The frame and/or tether can be removed after a desired amount of tissue ingrowth has occurred. This can further reduce the likelihood that the shape of the heart is affected due to contact with the frame and/or tether.

Other Embodiments

While certain embodiments have been described, these embodiments have been presented by way of example only, and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope of the disclosure. Accordingly, the scope of the present disclosure is defined only by reference to the claims presented herein or as presented in the future.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A system for replacing a native mitral valve, the system comprising:
   a replacement heart valve prosthesis;
   a frame shaped for placement on the exterior of a heart, the frame having a generally conical structure adapted for preserving a shape of the heart, the frame comprising two or more spaced-apart wings extending upwardly from a lower end of the frame; and
   a tether secured to the replacement heart valve prosthesis and slidably coupled to the frame,
   wherein the spaced-apart wings have a longitudinal length of between 4 cm and 10 cm and wherein the frame is shaped to extend upwardly from the lower end by at least 20 percent of a length of the heart.

2. The system of claim 1, wherein the frame is formed from a wire.

3. The system of claim 1, wherein at least some of the spaced-apart wings have different lengths.

4. The system of claim 1, wherein the spaced-apart wings are circumferentially spaced for placement between arteries of the heart.

5. The system of claim 1, wherein the anchor further comprises a tether adjustment mechanism configured to adjust a position of the tether relative to the frame, and wherein the tether adjustment mechanism is configured for wireless operation via a remote device.

6. The system of claim 5, wherein the tether adjustment mechanism comprises an electronic motor.

7. The system of claim 6, wherein the tether adjustment mechanism further comprises a piston configured to move relative to the frame, the tether being attached to the piston, wherein the electronic motor adjusts a position of the piston relative to the frame.

8. The system of claim 7, wherein the tether adjustment mechanism further comprises a magnetic ring operably coupled to the piston.

9. The system of claim 6, wherein the tether adjustment mechanism further comprises a receiver for receiving a wireless signal, wherein the wireless signal controls actuation of the electronic motor.

10. The system of claim 1, wherein the frame is sized and shaped for the lower end to engage an apex of the heart and to distribute loads along non-apical portions of the heart.

11. The system of claim 1, wherein the spaced-apart wings have a longitudinal length of at least 6 cm and wherein the frame is shaped to extend upwardly from the lower end by at least 30 percent of a length of the heart.

12. A system for replacing a native mitral valve, the system comprising:
   a replacement mitral valve prosthesis;
   a frame for placement on the exterior of a heart, the frame having a substantially conical shape adapted for preserving a shape of the heart, the frame comprising two or more wings extending upwardly from a lower end of the frame; and
   a tether secured to the replacement heart valve prosthesis and slidably coupled to the frame, the tether configured to also be attached to a leaflet of a native mitral valve,
   wherein the two or more wings have a longitudinal length of at least 6 cm and wherein the frame is shaped to extend upwardly from the lower end by at least 30 percent of a length of the heart.

13. The system of claim 12, wherein the frame is formed from a wire.

14. The system of claim 12, wherein the two or more wings consist of three spaced-apart wings.

15. The system of claim 14, wherein the three spaced-apart wings are circumferentially spaced for avoiding contact with coronary arteries of the heart.

16. The system of claim 12, wherein the anchor further comprises a tether adjustment mechanism configured to adjust a position of the tether relative to the frame, and wherein the tether adjustment mechanism is configured for wireless operation via a remote device.

17. The system of claim 16, wherein the tether adjustment mechanism includes a motor for adjusting a position of the tether.

18. The system of claim 17, wherein the motor is operated by a wireless signal.

19. The system of claim 12, wherein the frame is specifically tailored to conform to the patient's anatomy.

20. The system of claim 12, wherein the frame is collapsible.

* * * * *